United States Patent [19]

Imazio

[11] Patent Number: Plant 7,498

[45] Date of Patent: Apr. 16, 1991

[54] HEATHER PLANT NAMED ERICA 'AUGUSTINA'

[76] Inventor: Bruno L. Imazio, 197 Sunset Beach Rd., Watsonville, Calif. 95076

[21] Appl. No.: 393,674

[22] Filed: Aug. 14, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—James R. Cypher

[57] ABSTRACT

The present invention relates to a new and distinct cultivar of Heather plant named Erica Augustina, a seedling of unknown pollen parent growing in a field of *Erica persoluta* 'Sunset', the variety believed to be its seed parent, where it was selected because of its blooming habit which is earlier than that of any Heather variety familiar to me, long stems and attractive deep, rich rose-magenta color.

2 Drawing Sheets

BACKGROUND OF THE INVENTION

This invention relates to a new and distinct variety of the Ericaceae family which as been named Erica 'Augustina'. This new Heather variety was discovered by me in the Spring of 1985. I discovered thousands of little seedlings growing in between the plants and rows of a cultivated field of *Erica persoluta* 'Sunset' (U.S. Plant Pat. No. 5,336) in my commercial nursery at Watsonville, Calif. *Erica persoluta* 'Sunset' is believed to be the seed parent of the new variety and the pollen parent is unknown. Over a period of weeks these tiny seedlings, which had apparently germinated from seeds deposited by the *Erica persoluta* 'Sunset' plants the previous season, were dug up and potted and placed in a lath-house. By August of the same year, I began to plant the healthiest survivors of the "volunteer" seedlings in a field by themselves. Approximately 22,000 seedlings were planted.

In August of 1986, I found two plants from this field in full bloom. The plants were tall and have a beautiful rosy color. I kept the field of plants for another year and in August of 1987, I observed that the same two plants had retained the characteristics identified the previous year: color, length, and especially early blooming habit. Most significant was the blooming period, which predeeds the well-known variety Erica Regerminans by at least eight (8) weeks.

In January 1988, I selected one of the plants to propogate and named the new plant 'Augustina'. The plant was dug up and potted in a large container and placed in the lath-house to continue growing for propagative stock. By August 1988, I had over three thousand (3000) rooted plants, which has now resulted in a field of blooming plants of sufficient size to assure that the new variety will hold its novel characteristics.

The closest commercial cultivar to my new variety of which I am aware is the Heather Erica Regerminan. The distinguishing characteristics which are outstanding in the new cultivar and which distinguish it from Erica Regerminan are as follows:

1. Erica 'Augustina' blooms about mid-August, eight to ten weeks earlier than the closest commercial cultivar Erica Regerminans, which blooms in late October or early November.

2. Erica 'Augustina' is a deeper, richer, rose-magenta color than Erica Regerminan.

3. Erica 'Augustina' resembles Erica Regerminan in fragrance and in the size and shape of the bloom.

The geographic location where the 'Augustina' was discovered is along the temperate central coast of California. The soil is sandy and has a pH of approximately 5.6. 'Augustina' has been found to grow well in heavier clay soils with higher pH values also.

This new variety can also tolerate several hours of below-freezing temperatures, and seems to resist the powdery mildew which affects the *Erica persoluta* 'Sunset' heather and the persoluta heather.

The original 'Augustina' plant came from seed and I would presume they are also capable of producing seed. I have not looked for any seed since the 'Augustina' is propagated by cuttings.

The seed parent of the new variety is the *Erica persoluta* 'Sunset', but the pollen parent is not known; therefore I am not able to determine the species affiliation of 'Augustina'.

BRIEF DESCRIPTION OF THE DRAWING

The accompanying drawings serve by color photographic means, to illustrate the new plant variety, Erica 'Augustina', in comparison to its closest known commercial variety, Erica Regerminan. The photos were taken on Aug. 3, 1989 and the sky was overcast so the color representation is quite good.

DETAILED DESCRIPTION OF THE DRAWING

Figure 1:
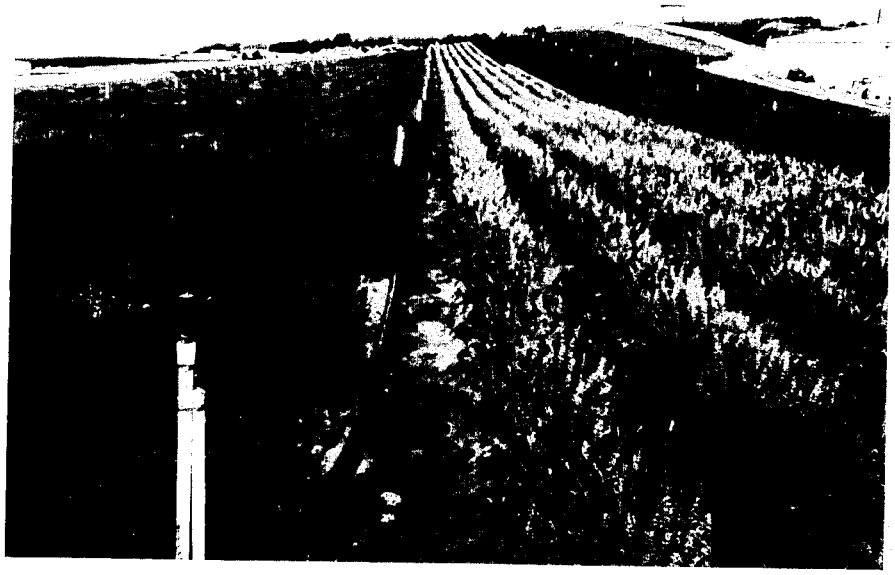
FIG. 1 shows a field of three different varieties of Heather. The green plants on the left are the variety Erica Regerminan, the blooming plants in the center are my new variety Erica 'Augustina', and the green plants on the right are the variety *Erica persoluta 'Sunset' (the seed parent). This photo shows the distinct difference in blooming time between the three varieties.*
Figure 2:
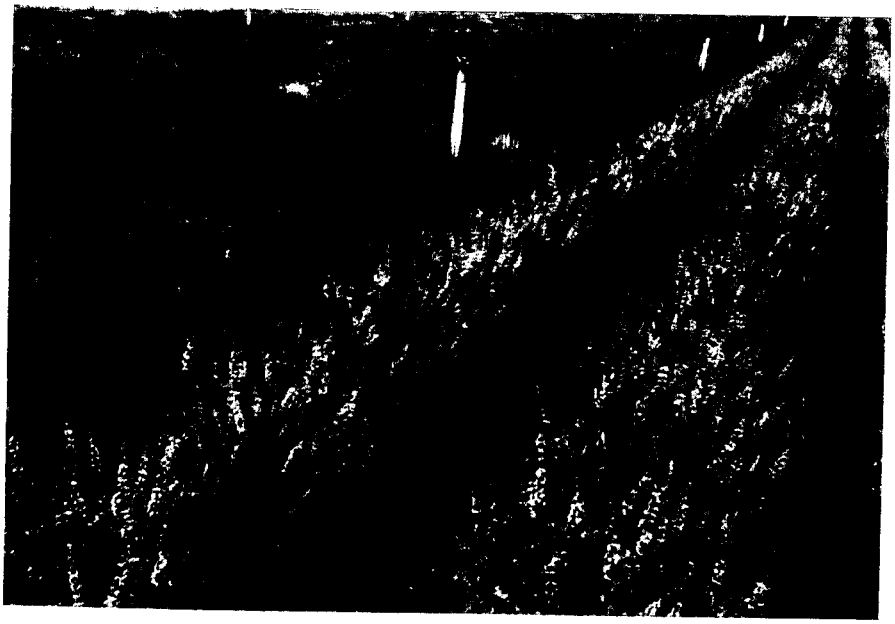
FIG. 2 is a close up view of the field showing the Erica regerminan on the left which is showing only slight, isolated blooms and my new variety Erica 'Augustina' on the right which is in full bloom. This photo illustrates the overall appearance of the new variety.
Figure 3:
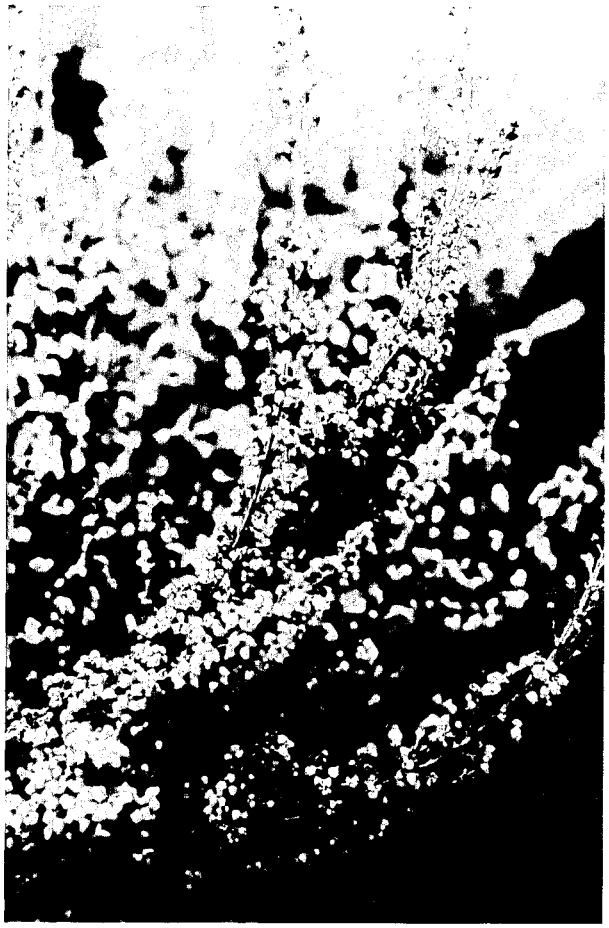
FIGS. 3 and 4 are close up views of my variety in the field showing the color and nature of its blossoms.
Figure 4:
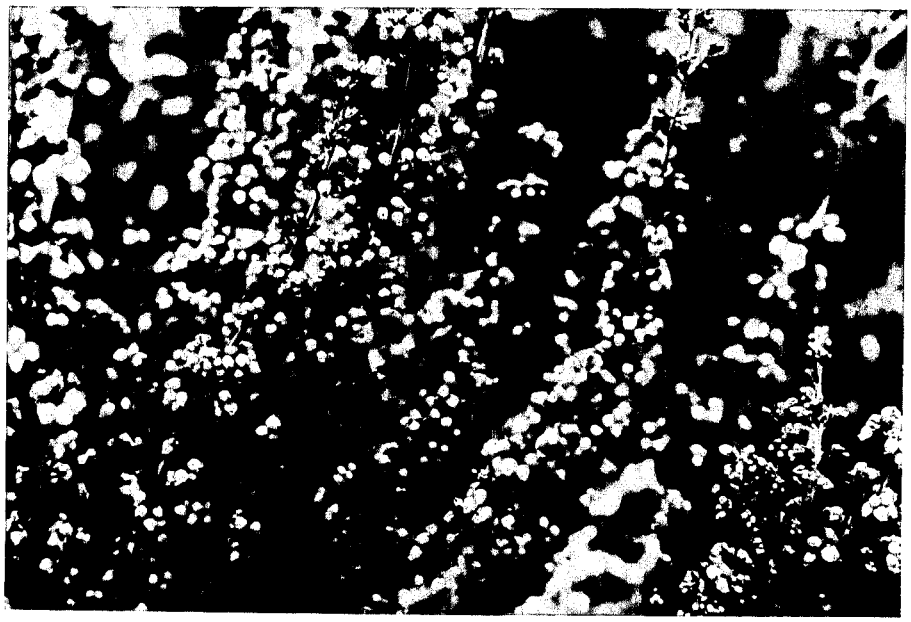

The following is a detailed description of my new Heather plant, Erica 'Augustina'based upon observations of field-grown plants in August 1989 at Watsonville, Calif. The color terminology used in the following is in accordance with The Royal Horticultural Society Colour Chart, the colors specified being as close as could reasonably be determined from the very small flowers of this plant.

PLANT

Origin: Seedling.
Parentage.
*Seed parent.*—*Erica persoluta* 'Sunset'.
Classification:
*Botanic.*—*Erica* 'Augustina'
*Commercial.*—'Augustina' Heather.
Form: Woody shrub, perennial.
Shape: Generally upright with stems curving slightly to accommodate fullness.
Height: About 2 feet.
Main stem length: Maximum 2 feet.
Branching: Generous, Pruned yearly to encourage fullness.
Growth: Upright with woody, flexible strength.
Foliage: Tiny needle-like leaves most dense on the flower bearing branches of main stems over entire plant.
*Size of leaf.*—⅛ to ¼ inch long, less than 1/16 inch wide.
*Shape.*—Long, narrow.
*Color.*—Mature foliage dark green (RHS 139A).
*Texture.*—Smooth.

THE BUD

Size: ⅛ inch or less diameter; ⅜ inch or less length.
Shape: Tear-drop with rounded base resting in calyx.
Color: RHS 70B.
Rate of opening: Progressive and continuous beginning at base of stem upwards to tip.

INFLORESCENCE

Blooming habit: Once annually, begining early August to mid-October.
Size of bloom: ⅛ inch diameter and length.
Borne: Compound raceme. Clusters with as many as twelve terminal buds.
Shape: Bell-shaped with pinched opening.
Appearance: Satiny.
Color: Dusty rose magenta, RHS 70B.
Flower stem:
*Length.*—¼ to 3 inches.
*Color.*—Light brown.
*Strength.*—Supple.
Fragrance: Mildly pungent.
Lasting quality:
*On plant.*—6 to 8 (approximately).
*As cut flower.*—Up to 4 weeks (approximation).
Discoloration: fades slightly.
Persistence: The bloom persists long after the stem ceases to draw water.
Effects of weather: Plant can tolerate freezing tempertures for several hours. Over 90 degree temperatures stress the plant. Extended periods of hot dry sunshine will accelerate blooming and cause blooms to fade and decline more quickly, shortening its lasting quality. Extended wet weather will cause more mature blooms in the clusters to turn brown.

I claim:

1. A new and distinct cultivar of Heather plant named Erica 'Augustina', substantially as herein shown and described characterized particularly as to novelty by its early blooming habit; attractive deep, rich rose-magenta color; and vigorous long stems desirable for cut flowers.

* * * * *